United States Patent
Matsuda et al.

(10) Patent No.: US 9,233,984 B2
(45) Date of Patent: Jan. 12, 2016

(54) COMPOUND, METHOD FOR PRODUCING COMPOUND, AND METHOD FOR PURIFYING COMPOUND

(71) Applicant: Nippon Soda Co., Ltd., Chiyoda-ku, Tokyo (JP)

(72) Inventors: Keiichiro Matsuda, Toyama (JP); Masayuki Matsushita, Toyama (JP); Kaoru Noda, Toyama (JP); Satoshi Kajita, Toyama (JP)

(73) Assignee: Nippon Soda Co., Ltd., Tokyo (JP)

(*) Notice: Subject to any disclaimer, the term of this patent is extended or adjusted under 35 U.S.C. 154(b) by 0 days.

(21) Appl. No.: 14/381,667

(22) PCT Filed: Mar. 6, 2013

(86) PCT No.: PCT/JP2013/056075
§ 371 (c)(1),
(2) Date: Aug. 28, 2014

(87) PCT Pub. No.: WO2013/137075
PCT Pub. Date: Sep. 19, 2013

(65) Prior Publication Data
US 2015/0045557 A1 Feb. 12, 2015

(30) Foreign Application Priority Data
Mar. 13, 2012 (JP) ................................. 2012-056136

(51) Int. Cl.
| C07D 257/04 | (2006.01) |
| C07D 257/10 | (2006.01) |
| C07D 403/00 | (2006.01) |
| C07D 487/00 | (2006.01) |
| C07F 1/02 | (2006.01) |
| C07D 401/12 | (2006.01) |
| C07F 1/00 | (2006.01) |
| A01N 43/713 | (2006.01) |

(52) U.S. Cl.
CPC ................ *C07F 1/02* (2013.01); *A01N 43/713* (2013.01); *C07D 257/04* (2013.01); *C07D 401/12* (2013.01); *C07F 1/00* (2013.01); *C07B 2200/13* (2013.01)

(58) Field of Classification Search
CPC .. C07D 257/04; C07D 403/10; C07D 401/10; C06B 43/00; C08G 18/3842
USPC .......................................................... 546/268
See application file for complete search history.

(56) References Cited

U.S. PATENT DOCUMENTS

| 8,273,781 B2 | 9/2012 | Suzuki et al. |
| 2005/0070439 A1 | 3/2005 | Kobori et al. |
| 2010/0137594 A1 | 6/2010 | Kobori et al. |
| 2011/0174527 A1 | 7/2011 | Nagamatsu et al. |
| 2012/0004420 A1* | 1/2012 | Suzumi ............... C07D 257/04 548/252 |
| 2013/0012713 A1 | 1/2013 | Miyazaki et al. |

FOREIGN PATENT DOCUMENTS

| JP | 2010-174008 A | 8/2010 |
| JP | 2010-174009 A | 8/2010 |
| JP | 2011-520778 A | 7/2011 |
| JP | 2011-236197 A | 11/2011 |
| WO | WO 03/016303 A1 | 2/2003 |
| WO | WO 2009/020191 A1 | 2/2009 |
| WO | WO 2009/115557 A2 | 9/2009 |
| WO | WO 2010/001597 A1 | 1/2010 |
| WO | WO 2010/103783 A1 | 9/2010 |
| WO | WO 2011/111831 A1 | 9/2011 |
| WO | WO 2013/117582 A1 | 8/2013 |

OTHER PUBLICATIONS

International Search Report dated Apr. 9, 2013, in PCT/JP2013/056075.
Office Action mailed Jun. 3, 2015, in CN 201380011176.0.
Supplementary European Search Report dated Sep. 16, 2015, in EP 13760384.1.

* cited by examiner

*Primary Examiner* — Nyeemah A Grazier
*Assistant Examiner* — Sagar Patel
(74) *Attorney, Agent, or Firm* — Foley & Lardner LLP

(57) ABSTRACT

The present invention provides a compound characterized by being represented by general formula (I):

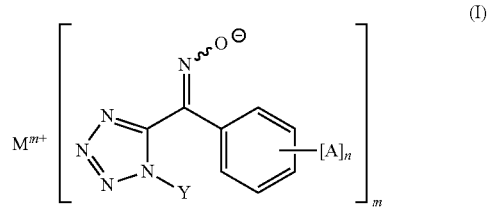

(wherein, A represents a halogen atom, alkyl group, haloalkyl group, alkoxy group, haloalkoxy group, alkylsulfonyl group, unsubstituted or substituted aryl group, cyano group or nitro group, n represents an integer of 0 to 5 (and A may be mutually the same or different when n is 2 or more), Y represents an alkyl group, M represents an alkaline metal or alkaline earth metal, and m represents an integer of 1 or 2).

11 Claims, No Drawings

COMPOUND, METHOD FOR PRODUCING COMPOUND, AND METHOD FOR PURIFYING COMPOUND

CROSS-REFERENCE TO RELATED APPLICATIONS

This application is a National Stage application of PCT/JP2013/056075, filed Mar. 6, 2013, which claims priority from Japanese application JP 2012-056136, filed Mar. 13, 2012.

TECHNICAL FIELD

The present invention relates to a compound that is a salt of a tetrazolylhydroxyimino derivative, a method for purifying a specific geometrical isomer of the aforementioned compound, and a method for producing a tetrazolyloxime derivative using the aforementioned compound.

The present application claims priority on the basis of Japanese Patent Application No. 2012-056136, filed in Japan on Mar. 13, 2012, the contents of which are incorporated herein by reference.

BACKGROUND ART

Numerous control agents have been proposed for use against diseases of agricultural and horticultural crops. For example, Patent Document 1 discloses a tetrazolyloxime derivative (general formula (P)) that has superior pharmacological efficacy for useful plants, and proposes the use of that derivative as a plant disease control agent.

[Chemical Formula 1]

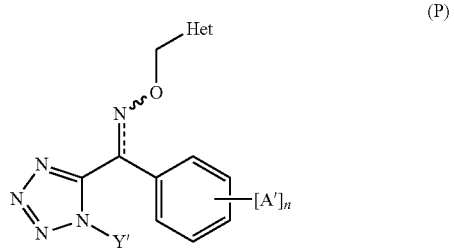

(P)

In general formula (P), A' represents a halogen atom, alkyl group, alkoxy group, methanesulfonyl group, trifluoromethyl group, aryl group, cyano group or nitro group, n represents an integer of 0 to 5, Y' represents an alkyl group, and Het represents a substituted pyridyl group or substituted thiazolyl group. Furthermore, in general formula (P), "N~O" indicates that the aforementioned oxime moiety may be of the (E) form or (Z) form.

[Chemical Formula 2]

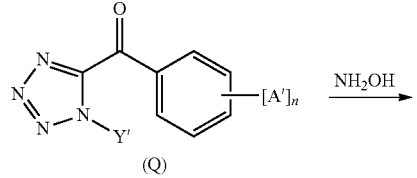

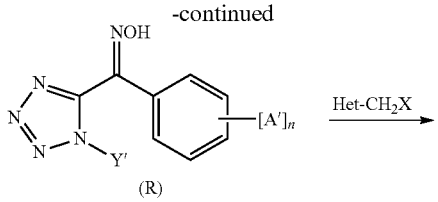

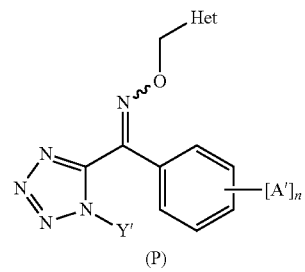

The tetrazolyloxime derivative represented by this general formula (P) can be produced by obtaining a tetrazolylhydroxyimino derivative represented by general formula (R) by reacting hydroxylamine with a 1-alkyl-5-benzoyl-1H-tetrazole derivative represented by general formula (Q), and then reacting this with Het-CH$_2$X (wherein, X represents a chlorine atom, bromine atom or iodine atom) in the presence of a base (such as sodium hydride, sodium hydroxide, potassium hydroxide, sodium carbonate, potassium carbonate, cesium carbonate, triethylamine, pyridine or N,N-dimethylaminopyridine). Furthermore, the 1-alkyl-5-benzoyl-1H-tetrazole derivative represented by general formula (Q) can be synthesized by, for example, the method disclosed in Patent Document 2. In addition, a halogenated picoline derivative described in Patent Document 3, for example, can be used for the Het-CH$_2$X.

The tetrazolyloxime derivative represented by general formula (P) has (E) form and (Z) form stereoisomers based on the carbon-nitrogen double bond of the oxime moiety. Although both the (Z) form and (E) form have activity, the (Z) form is preferable.

PRIOR ART DOCUMENTS

Patent Documents

Patent Document 1: International Publication No. WO 2003/016303
Patent Document 2: International Publication No. WO 2010/001597
Patent Document 3: International Publication No. WO 2011/111831

DISCLOSURE OF THE INVENTION

Problems to be Solved by the Invention

Tetrazolyloxime derivatives represented by general formula (P) are normally obtained as a mixture of the (E) form and (Z) form. Consequently, in order to obtain only the (Z) form, a mixture of the (E) form and (Z) form must be subjected to a purification step such as separating and refining by silica gel column chromatography.

On the other hand, in order to synthesize only the (Z) form in the synthesis of a tetrazolyloxime derivative represented by general formula (P), it is preferable to only use the (Z) form of the aforementioned tetrazolylhydroxyimino derivative represented by general formula (R) as raw material. However, since the tetrazolylhydroxyimino derivative represented by general formula (R) is also normally obtained as a mixture of the (E) form and the (Z) form, a purification step is similarly required in order to obtain only the (Z) form.

An object of the present invention is to provide a compound that is preferable as a synthesis intermediate for producing the (Z) form of a tetrazolyloxime derivative represented by general formula (P) at high purity by inhibiting the amount of (E) form present therein, and a method for producing the aforementioned compound.

Means for Solving the Problems

As a result of conducting extensive studies to solve the aforementioned problems, the inventors of the present invention found that the crystallization efficiency of the (Z) form recovered as a crystal can be remarkably enhanced by alcohol crystallization by converting the aforementioned tetrazolylhydroxyimino derivative represented by general formula (R) to an alkaline metal salt or alkaline earth metal salt, and that the reaction rates of the photoisomerization reactions of these salts are faster than that of the aforementioned tetrazolylhydroxyimino derivative, enabling equilibrium to be reached in a short period of time, and thereby leading to completion of the present invention.

Namely, the compound of the present invention, method for producing that compound, method for purifying the (Z) form of that compound, and method for producing the (Z) form of that compound are as described in [1] to [11] below.

[1] A compound represented by general formula (I):

[Chemical Formula 3]

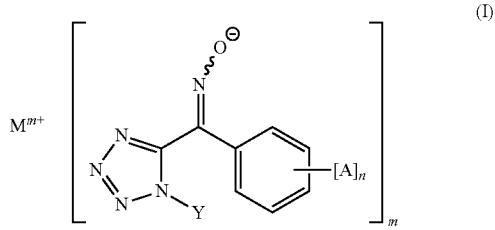

(wherein, A represents a halogen atom, alkyl group, haloalkyl group, alkoxy group, haloalkoxy group, alkylsulfonyl group, unsubstituted or substituted aryl group, cyano group or nitro group, n represents an integer of 0 to 5 (and A may be mutually the same or different when n is 2 or more), Y represents an alkyl group, M represents an alkaline metal or alkaline earth metal, and m represents an integer of 1 or 2).

[2] The compound of [1] above, which is a (Z) form.

[3] The compound of [1] or [2] above, which contains 2 molecules of water per molecule thereof.

[4] The compound of any of [1] to [3] above, wherein M is an alkaline metal.

[5] A method for producing the compound represented by general formula (I), which includes a step (A) for allowing an alkaline metal compound or alkaline earth metal compound to act on a tetrazolyloxime derivative represented by general formula (II):

[Chemical Formula 4]

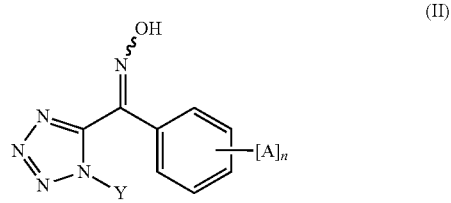

(wherein, A represents a halogen atom, alkyl group, haloalkyl group, alkoxy group, haloalkoxy group, alkylsulfonyl group, unsubstituted or substituted aryl group, cyano group or nitro group, n represents an integer of 0 to 5 (and A may be mutually the same or different when n is 2 or more), and Y represents an alkyl group).

[6] A method for purifying the (Z) form of a compound represented by general formula (I), which includes a step (B) for crystallizing crystals of the (Z) form of a compound represented by general formula (I) by adding an alcohol to an aqueous solution of the compound represented by general formula (I).

[7] The purification method of [6] above, wherein the alcohol is a lower alcohol.

[8] A method for producing the (Z) form of a compound represented by general formula (I), which includes a step (C) for irradiating a solution containing the (E) form of the compound represented by general formula (I) with light and isomerizing to the (Z) form.

[9] The method for producing the (Z) form of a compound represented by general formula (I) of [8] above, which includes:

a step (C'), in which the solution containing the (E) form of the compound represented by general formula (I) is an aqueous solution, and a step (B') for precipitating crystals of the (Z) form of the compound represented by general formula (I) by adding an alcohol to the aqueous solution following the step (C').

[10] A method for producing a tetrazolyloxime derivative represented by general formula (IV), which includes a step (D1) for obtaining a tetrazolyloxime derivative represented by general formula (IV) by reacting the compound represented by general formula (I) with a halide represented by general formula (III):

[Chemical Formula 5]

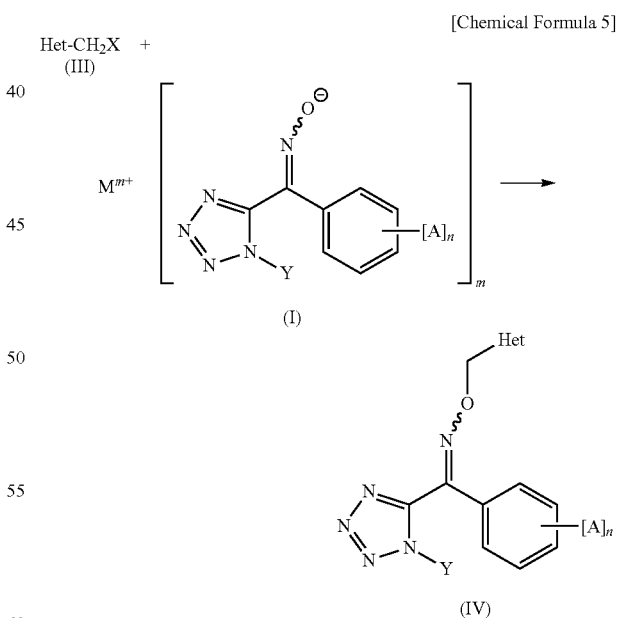

(wherein, in general formula (III), Het represents a substituted pyridyl group or substituted thiazolyl group, and X represents a halogen atom, and in general formula (IV), Het, X, A, n and Y are respectively the same as previously defined in general formula (III) and general formula (I)).

[11] The method for producing the tetrazolyloxime derivative represented by general formula (IV) of [10] above, wherein the halide compound represented by general formula (III) is a halogenated picoline derivative represented by general formula (VI):

[Chemical Formula 6]

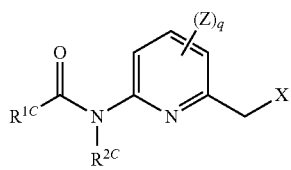

(wherein,
$R^{1C}$ represents an unsubstituted or substituted alkyl group or unsubstituted or substituted alkoxy group,
$R^{2C}$ represents a hydrogen atom, unsubstituted or substituted alkoxycarbonyl group or unsubstituted or substituted acyl group,
X represents a halogen atom,
Z represents a halogen atom, cyano group, nitro group, hydroxyl group, thiol group, formyl group, carboxyl group, unsubstituted or substituted amino group, unsubstituted or substituted alkyl group, unsubstituted or substituted alkenyl group, unsubstituted or substituted alkynyl group, unsubstituted or substituted aryl group, unsubstituted or substituted heterocyclic group, $OR^3$, $S(O)_pR^3$, $COR^3$ or $CO_2R^3$ (wherein, $R^3$ represents an unsubstituted or substituted amino group, unsubstituted or substituted alkyl group, unsubstituted or substituted alkenyl group, unsubstituted or substituted alkynyl group, unsubstituted or substituted aryl group or unsubstituted or substituted heterocyclic group, and p indicates the number of oxygen atoms shown in parentheses and is an integer of 0 to 2), and
q indicates the number of substituents Z and is an integer of 0 to 3, and a plurality of Z may be mutually the same or different when q is 2 or more).

Effects of the Invention

The (Z) form among geometrical isomers of the compound of the present invention can be easily separated and purified from the (E) form. In addition, the (Z) form of the compound of the present invention can be obtained from the (E) form both easily and in a short period of time by a photoisomerization reaction. Consequently, the compound of the present invention is particularly useful as a synthesis intermediate for synthesizing tetrazolyloxime derivatives that are useful as active ingredients of agricultural chemicals and the like, and the use of the aforementioned compound makes it possible to produce the (Z) form of a tetrazolyloxime derivative both easily and at high purity.

BEST MODE FOR CARRYING OUT THE INVENTION

Although the following provides an explanation of preferable examples of the present invention, the present invention is not limited to these examples. Constituents of the present invention can be added, omitted, substituted or modified in other ways within a range that does not deviate from the gist of the present invention.

<Compound Represented by General Formula (I)>
The compound of the present invention is characterized in that it is represented by general formula (I):

[Chemical Formula 7]

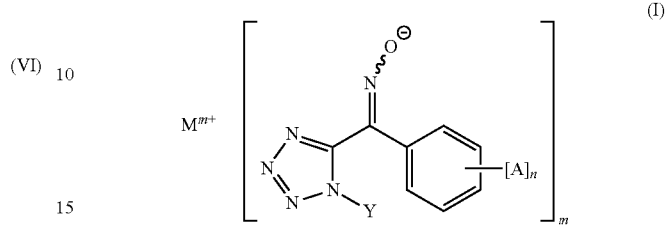

(wherein, A represents a halogen atom, alkyl group, haloalkyl group, alkoxy group, haloalkoxy group, alkylsulfonyl group, unsubstituted or substituted aryl group, cyano group or nitro group, n represents an integer of 0 to 5 (and A may be mutually the same or different when n is 2 or more), Y represents an alkyl group, M represents an alkaline metal or alkaline earth metal, and m represents an integer of 1 or 2).

In general formula (I), A represents a halogen atom, alkyl group, haloalkyl group, alkoxy group, haloalkoxy group, alkylsulfonyl group, unsubstituted or substituted aryl group, cyano group or nitro group.

Examples of halogen atoms include a fluorine atom, chlorine atom, bromine atom and iodine atom.

Examples of alkyl groups include a methyl group, ethyl group, n-propyl group, i-propyl group, n-butyl group, i-butyl group, s-butyl group, t-butyl group, n-pentyl group and n-hexyl group. The number of carbon atoms that compose the alkyl group is preferably 1 to 8.

Examples of haloalkyl groups include a fluoromethyl group, chloromethyl group, bromomethyl group, difluoromethyl group, dichloromethyl group, trifluoromethyl group, trichloromethyl group, trifluoroethyl group, pentafluoroethyl group, 3,3,3,2,2-pentafluoropropyl group and 2,2,2-trifluoro-1-trifluoromethylethyl group. The number of carbon atoms that compose the haloalkyl group is preferably 1 to 8.

Examples of alkoxy groups include a methoxy group, ethoxy group, n-propoxy group, i-propoxy group, n-butoxy group, i-butoxy group, s-butoxy group, t-butoxy group and n-hexyloxy group. The number of carbon atoms that compose the alkoxy group is preferably 1 to 8.

Examples of haloalkoxy groups include a 2-chloro-n-propoxy group, 2,3-dichlorobutoxy group and trifluoromethoxy group. The number of carbon atoms that compose the haloalkoxy group is preferably 1 to 8.

Examples of alkylsulfonyl groups include a methylsulfonyl group, ethylsulfonyl group, n-propylsulfonyl group, i-propylsulfonyl group and t-butylsulfonyl group. The number of carbon atoms that compose the alkylsulfonyl group is preferably 1 to 8.

An aryl group refers to a monocyclic or polycyclic aryl group. Furthermore, polycyclic aryl groups are such that, provided at least one of the rings is an aromatic ring, the remaining rings may be saturated rings, unsaturated rings or aromatic rings. Aryl groups having 6 to 10 carbon atoms are preferable.

Specific examples of unsubstituted aryl groups include a phenyl group, 1-naphthyl group, 2-naphthyl group, azulenyl group, indanyl group and tetralinyl group.

There are no particular limitations on the substituent in a substituted aryl group provided it is a chemically acceptable group. More specifically, examples of substituents include those indicated below.

(1) halogen atoms such as a fluorine atom, chlorine atom, bromine atom or iodine atom; (2) alkyl groups such as a methyl group, ethyl group, n-propyl group, i-propyl group, n-butyl group, s-butyl group, i-butyl group, t-butyl group, n-pentyl group or n-hexyl group; (3) cycloalkyl groups such as a cyclopropyl group, cyclobutyl group, cyclopentyl group, cyclohexyl group or cycloheptyl group; (4) alkoxy groups such as a methoxy group, ethoxy group, n-propoxy group, i-propoxy group, n-butoxy group, i-butoxy group, s-butoxy group or t-butoxy group; (5) alkenyl groups such as a vinyl group, 1-propenyl group, 2-propenyl group, 1-butenyl group, 2-butenyl group, 3-butenyl group, 1-methyl-2-propenyl group, 2-methyl-2-propenyl group, 1-pentenyl group, 2-pentenyl group, 3-pentenyl group, 4-pentenyl group, 1-methyl-2-butenyl group, 2-methyl-2-butenyl group, 1-hexenyl group, 2-hexenyl group, 3-hexenyl group, 4-hexenyl group or 5-hexenyl group;

(6) cycloalkenyl groups such as a 2-cyclopropenyl group, 2-cyclopentenyl group, 3-cyclohexenyl group or 4-cyclooctenyl group; (7) alkenyloxy groups such as a vinyloxy group, allyloxy group, 1-propenyloxy group or 2-butenyloxy group; (8) alkynyl groups such as ethynyl group, 1-propynyl group, 2-propynyl group, 1-butynyl group, 2-butynyl group, 3-butynyl group, 1-methyl-2-propynyl group, 2-methyl-3-butynyl group, 1-pentynyl group, 2-pentynyl group, 3-pentynyl group, 4-pentynyl group, 1-methyl-2-butynyl group, 2-methyl-3-pentynyl group, 1-hexynyl group or 1,1-dimethyl-2-butynyl group; (9) alkynyloxy groups such as an ethynyloxy group or propargyloxy group; (10) aryl groups such as a phenyl group, 1-naphthyl group or 2-naphthyl group;

(11) aryloxy groups such as a phenoxy group or 1-napthoxy group; (12) aralkyl groups such as a benzyl group or phenethyl group; (13) aralkyloxy groups such as a benzyloxy group or phenethyloxy group; (14) acyl groups such as a formyl group, acetyl group, propionyl group, benzoyl group, cyclohexylcarbonyl group or phthaloyl group; (15) alkoxycarbonyl groups such as a methoxycarbonyl group, ethoxycarbonyl group, n-propoxycarbonyl group, i-propoxycarbonyl group, n-butoxycarbonyl group or t-butoxycarbonyl group; (16) carboxyl groups; (17) hydroxyl groups; (18) haloalkyl groups such as a chloromethyl group, chloroethyl group, 1,2-dichloro-n-propyl group, 1-fluoro-n-butyl group or perfluoro-n-pentyl group; (19) haloalkoxy groups such as a 2-chloro-n-propoxy group, 2,3-dichlorobutoxy group or trifluoromethoxy group; (20) haloalkenyl groups such as a 2-chloro-1-propenyl group or 2-fluoro-1-butenyl group; (21) haloalkynyl groups such as a 4,4-dichloro-1-butynyl group, 4-fluoro-1-pentynyl group or 5-bromo-2-pentynyl group;

(22) haloalkenyloxy groups such as a 2-chloro-1-propenyloxy group or 3-bromo-2-butenyloxy group; (23) haloalkynyl groups such as a 3-chloro-propargyl group or 3-iodo-propargyl group; (24) haloalkynyloxy groups such as a 3-chloro-propargyloxy group or 3-iodo-propargyloxy group; (25) haloaryl groups such as a 4-chlorophenyl group, 4-fluorophenyl group or 2,4-dichlorophenyl group; (26) haloaryloxy groups such as a 4-fluorophenoxy group or 4-chloro-1-naphthoxy group; (27) halogen-substituted acyl groups such as a chloroacetyl group, trifluoroacetyl group, trichloroacetyl group or 4-chlorobenzoyl group; (28) alkoxyalkyl groups such as a methoxymethyl group, ethoxymethyl group, 1-ethoxyethyl group or 2-ethoxyethyl group; (29) alkoxyalkoxy groups such as a methoxymethoxy group, ethoxymethoxy group, 1-ethoxyethoxy group or 2-ethoxyethoxy group; (30) cyano groups;

(31) isocyano groups; (32) nitro groups; (33) isocyanato groups; (34) cyanato groups; (35) amino groups ($NH_2$ groups); (36) alkylamino groups such as a methylamino group, dimethylamino group or diethylamino group; (37) arylamino groups such as a anilino group, naphthylamino group or anthranylamino group; (38) aralkylamino groups such as benzylamino group or phenethylamino group; (39) alkylsulfonylamino groups such as a methylsulfonylamino group, ethylsulfonylamino group, n-propylsulfonylamino group, i-propylsulfonylamino group or n-butylsulfonylamino group; (40) arylsulfonylamino groups such as a phenylsulfonylamino group;

(41) heteroarylsulfonylamino groups such as a pyrazinylsulfonylamino group; (42) acylamino groups such as a formylamino group, acetylamino group, propanoylamino group, butyrylamino group, i-propylcarbonylamino group or benzoylamino group; (43) alkoxycarbonylamino groups such as a methoxycarbonylamino group or ethoxycarbonylamino group; (44) haloalkylsulfonylamino groups such as a fluoromethylsulfonylamino group, chloromethylsulfonylamino group, bromomethylsulfonylamino group, difluoromethylsulfonylamino group, dichloromethylsulfonylamino group, 1,1-difluoroethylsulfonylamino group, trifluoromethylsulfonylamino group, 2,2,2-trifluoroethylsulfonylamino group or pentafluoroethylsulfonylamino group; (45) bis(alkylsulfonyl)amino groups such as a bis(methylsulfonyl)amino group, bis(ethylsulfonyl)amino group, (ethylsulfonyl)(methylsulfonyl)amino group, bis(n-propylsulfonyl)amino group, bis(i-propylsulfonyl)amino group, bis(n-butylsulfonyl)amino group or bis(t-butylsulfonyl)amino group;

(46) bis(haloalkylsulfonyl)amino groups such as a bis(fluoromethylsulfonyl)amino group, bis(chloromethylsulfonyl)amino group, bis(bromomethylsulfonyl)amino group, bis(dichloromethylsulfonyl)amino group, bis(1,1-difluoroethylsulfonyl)amino group, bis(trifluoromethylsulfonyl)amino group, bis(2,2,2-trifluoroethylsulfonyl)amino group or bis(pentafluoroethylsulfonyl)amino group; (47) unsubstituted or substituted hydrazino groups such as a hydrazino group, N'-phenylhydrazino group, N'-methoxycarbonylhydrazino group, N'-acetylhydrazino group or N'-methylhydrazino group; (48) unsubstituted or substituted aminocarbonyl groups such as an aminocarbonyl group, dimethylaminocarbonyl group, phenylaminocarbonyl group or N-phenyl-N-methylaminocarbonyl group; (49) unsubstituted or substituted hydrazinocarbonyl groups such as a hydrazinocarbonyl group, N'-methylhydrazinocarbonyl group or N'-phenylhydrazinocarbonyl group; (50) unsubstituted or substituted iminoalkyl groups such as an N-methyliminomethyl group, 1-N-phenyliminoethyl group, N-hydroxyiminomethyl group or N-methoxyiminomethyl group;

(51) thiol groups; (52) isothiocyanato groups; (53) thiocyanato groups; (54) alkylthio groups such as a methylthio group, ethylthio group, n-propylthio group, i-propylthio group, n-butylthio group, i-butylthio group, s-butylthio group or t-butylthio group; (55) alkenylthio groups such as a vinylthio group or allylthio group; (56) alkynylthio groups such as a ethynylthio group or propargylthio group; (57) arylthio groups such as a phenylthio group or naphthylthio group; (58) heteroarylthio groups such as a 2-pyridylthio group or 3-pyridazylthio group; (59) aralkylthio groups such as a benzylthio group or phenethylthio group; (60) heteroaralkylthio groups such as a 2-pyridylmethylthio group or 2-furylmethylthio group; (61) alkylthiocarbonyl groups such as a methylthiocarbonyl group, ethylthiocarbonyl group, n-propylthiocarbonyl group, i-propylthiocarbonyl group, n-butylthiocarbonyl group, i-butylthiocarbonyl group, s-butylthiocarbonyl group or t-butylthiocarbonyl group;

(62) alkylthioalkyl groups such as a methylthiomethyl group or 1-methylthioethyl group; (63) arylthioalkyl groups such as a phenylthiomethyl group or 1-phenylthioethyl group; (64) alkylthioalkoxy groups such as a methylthiomethoxy group or 1-methylthioethoxy group; (65) arylthioalkoxy groups such as a phenylthiomethoxy group or 1-phenylthioethoxy group; (66) alkylsulfinyl groups such as a methylsulfinyl group, ethylsulfinyl group or t-butylsulfinyl group; (67) alkenylsulfinyl groups such as a allylsulfinyl group; (68) alkynylsulfinyl groups such as a propargylsulfinyl group; (69) arylsulfinyl groups such as a phenylsulfinyl group; (70) heteroarylsulfinyl groups such as a 2-pyridylsulfinyl group or 3-pyridylsulfinyl group; (71) aralkylsulfinyl groups such as a benzylsulfinyl group or phenethylsulfinyl group; (72) heteroarylalkylsulfinyl groups such as a 2-pyridylmethylsulfinyl group or 3-pyridylmethylsulfinyl group;

(73) alkylsulfonyl groups such as a methylsulfonyl group, ethylsulfonyl group or t-butylsulfonyl group; (74) alkenylsulfonyl groups such as a allylsulfonyl group; (75) alkynylsulfonyl groups such as a propargylsulfonyl group; (76) arylsulfonyl groups such as a phenylsulfonyl group; (77) heteroarylsulfonyl groups such as a 2-pyridylsulfonyl group or 3-pyridylsulfonyl group; (78) aralkylsulfonyl groups such as a benzylsulfonyl group or phenethylsulfonyl group; (79) heteroarylalkylsulfonyl groups such as a 2-pyridylmethylsulfonyl group or 3-pyridylmethylsulfonyl group; (80) unsaturated five-membered heterocyclic groups such as a furan-2-yl group, furan-3-yl group, thiophen-2-yl group, thiophen-3-yl group, pyrrol-2-yl group, pyrrol-3-yl group, oxazol-2-yl group, oxazol-4-yl group, oxazol-5-yl group, thiazol-2-yl group, thiazol-4-yl group, thiazol-5-yl group, isoxazol-3-yl group, isoxazol-4-yl group, isoxazol-5-yl group, isothiazol-3-yl group, isothiazol-4-yl group, isothiazol-5-yl group, imidazol-2-yl group, imidazol-4-yl group, imidazol-5-yl group, pyrazol-3-yl group, pyrazol-4-yl group, pyrazol-5-yl group, 1,3,4-oxadiazol-2-yl group, 1,3,4-thiadiazol-2-yl group, 1,2,3-triazol-4-yl group, 1,2,4-triazol-3-yl group or 1,2,4-triazol-5-yl group;

(81) unsaturated 6-membered heterocyclic groups such as a pyridin-2-yl group, pyridin-3-yl group, pyridin-4-yl group, 5-chloro-3-pyridyl group, 3-trifluoromethyl-2-pyridyl group, pyridazin-3-yl group, pyridazin-4-yl group, pyrazin-2-yl group, pyrimidin-5-yl group, 1,3,5-triazin-2-yl group or 1,2,4-triazin-3-yl group; (82) saturated or partially unsaturated heterocyclic groups such as a tetrahydrofuran-2-yl group, tetrahydropyran-4-yl group, piperidin-3-yl group, pyrrolidin-2-yl group, morpholino group, piperidino group, N-methylpiperazino group or oxazolin-2-yl group; (83) heterocyclooxy groups such as 2-pyridyloxy group or 3-isooxazolyloxy group; (84) heteroarylalkyl groups such as a 2-pyridylmethyl group or 3-pyridylmethyl group; and, (85) heteroarylalkoxy groups such as a 2-pyridylmethoxy group or 3-pyridylmethoxy group.

These substituents exemplified in (1) to (85) can further have the substituents exemplified in (1) to (85) within a chemically acceptable range.

Specific examples of substituted aryl groups include a 4-fluorophenyl group, 4-chlorophenyl group, 2,4-dichlorophenyl group, 3,4-dichlorophenyl group, 3,5-dichlorophenyl group, 2,6-difluorophenyl group, 4-trifluoromethylphenyl group, 4-methoxyphenyl group, 3,4-dimethoxyphenyl group, 3,4-methylenedioxyphenyl group, 4-trifluoromethoxyphenyl group and 4-methoxy-1-naphthyl group.

Among these, A is preferably a halogen atom.

In general formula (I), n represents an integer of 0 to 5, preferably represents an integer of 0 to 3, and more preferably represents 0. Furthermore, A may be mutually the same or different when n is 2 or more.

In general formula (I), Y represents an alkyl group. Examples of alkyl groups include a methyl group, ethyl group, n-propyl group, i-propyl group, n-butyl group, i-butyl group, s-butyl group, t-butyl group, n-pentyl group and n-hexyl group. Among these, Y preferably represents an alkyl group having 1 to 6 carbon atoms, more preferably represents an alkyl group having 1 to 3 carbon atoms, and particularly preferably represents a methyl group.

In general formula (I), M represents an alkaline metal or alkaline earth metal. Examples of alkaline metals include sodium, potassium and lithium, while examples of alkaline earth metals include magnesium and calcium. Among these, M is preferably sodium or potassium and more preferably sodium.

In general formula (I), m represents an integer of 1 or 2. m is 1 in the case M represents an alkaline metal, while m is 2 in the case M represents an alkaline earth metal.

The compound represented by general formula (I) of the present invention is preferably a compound in which A is a halogen atom, n is an integer of 0 to 3, Y is an alkyl group having 1 to 6 carbon atoms, M is sodium, potassium, lithium, magnesium or calcium, and m is an integer of 1 or 2, more preferably a compound in which n is 0, Y is an alkyl group of 1 to 6 carbon atoms, M is sodium, potassium, lithium, magnesium or calcium and m is an integer of 1 or 2, even more preferably a compound in which n is 0, Y is an alkyl group having 1 to 6 carbon atoms, M is sodium or potassium and m is 1, still more preferably a compound in which n is 0, Y is an alkyl group having 1 to 3 carbon atoms, M is sodium or potassium and m is 1, and particularly preferably a compound in which n is 0, Y is an alkyl group having 1 to 3 carbon atoms, M is sodium and m is 1.

A compound represented by general formula (I) has geometrical isomers consisting of an (E) form (represented by the following general formula (I-E)) and a (Z) form (represented by the following general formula (I-Z)). In the invention of the present application and description of the present application, both the (E) form and the (Z) form are included in compounds represented by general formula (I) unless specifically indicated otherwise. Namely, a compound represented by general formula (I) may be the (E) form or the (Z) form.

[Chemical Formula 8]

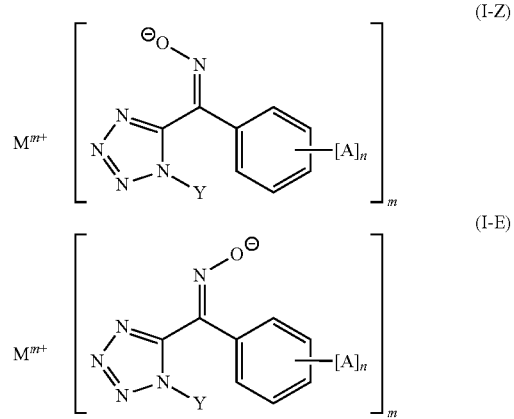

In addition, hydrates, various types of solvates, crystal polymorphs and the like are also included in compounds represented by general formula (I). The compound represented by general formula (I) of the present invention preferably contains water molecules in the manner of a hydrate and the like, and more preferably contains two molecules of water molecules. For example, a crystal of the compound represented by general formula (I) of the present invention contains two molecules of crystalline water per molecule thereof. Crystals containing these two molecules of water molecules have greater thermal stability than crystals of the tetrazolyloxime derivative represented by general formula (II) to be subsequently described.

<Method for Producing Compound Represented by General Formula (I)>

The compound represented by general formula (I) can be synthesized from a known compound using a known chemical reaction.

For example, the compound represented by formula (I) can be produced by a step (A) for allowing an alkaline metal compound or alkaline earth metal compound to act on a tetrazolyloxime derivative represented by general formula (II):

[Chemical Formula 9]

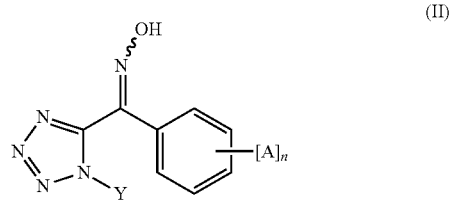

(II)

(wherein, A, n and Y represent alkyl groups).

The tetrazolyloxime derivative represented by general formula (II) can be synthesized from a known compound using a known chemical reaction. More specifically, an example of a method for synthesizing the tetrazolyloxime derivative represented by general formula (II) consists of reacting hydroxylamine with a 1-alkyl-5-benzoyl-1H-tetrazole derivative (see, for example, Patent Document 2).

Specific examples of alkaline metal compounds and alkaline earth metal compounds used in step (A) include alkaline metal hydroxides such as sodium hydroxide, potassium hydroxide or lithium hydroxide, alkaline earth metal hydroxides such as magnesium hydroxide or calcium hydroxide, carbonates such as sodium carbonate, potassium carbonate, lithium carbonate, magnesium carbonate, calcium carbonate, sodium bicarbonate or potassium bicarbonate, hydrides such as sodium hydride, lithium hydride or calcium hydride, and metal alkoxides such as sodium methoxide, sodium ethoxide or magnesium methoxide. Among these, alkaline metal hydroxides are preferable.

There are no particular limitations on the solvent used in the reaction of step (A) provided it is a solvent that is able to dissolve any of the tetrazolyloxime derivative represented by general formula (II), the alkaline metal compound or alkaline earth metal compound, and the compound represented by general formula (I). The solvent in step (A) is preferably water or a lower alcohol.

The temperature of the reaction of step (A) can be suitably set in consideration of such factors as the type of solvent used. For example, the reaction temperature in the case of using water for the solvent is 0° C. to 100° C., preferably 20° C. to 80° C. and more preferably 40° C. to 80° C. Although varying according to such factors as the reaction scale, the reaction time is normally 15 minutes to 24 hours.

<Method for Purifying (Z) Form of Compound Represented by General Formula (I)>

The (Z) form of the compound represented by general formula (I) of the present invention can be preferentially crystallized over the (E) form in the case of crystallization using alcohol as a poor solvent. This can be utilized to purify the compound represented by general formula (I) by separating the (Z) form from the (E) form. The crystallization yield of the (Z) form is higher for the compound represented by general formula (I) than the tetrazolyloxime derivative represented by general formula (II). Consequently, producing the compound represented by general formula (I) followed by crystallization thereof allows the (Z) form to be obtained at higher purity (namely, having a lower level of contamination by the (E) form) than crystallizing the tetrazolyloxime derivative represented by general formula (II) directly.

More specifically, the (Z) form can be purified by a step (B) for crystallizing the (Z) form of the compound represented by general formula (I) by adding an alcohol to an aqueous solution of the compound represented by general formula (I).

In step (B), although the aqueous solution to which the alcohol is added is only required to be the compound represented by general formula (I) that at least contains the (Z) form, it preferably contains both the (Z) form and the (E) form of the compound represented by general formula (I). In this case, the majority of the (Z) form (for example, 95% or more and preferably 98% or more) is crystallized while nearly all of the (E) form remains dissolved in the mother liquor. In the present invention, since the crystallization efficiency of the (Z) form is extremely high, the (Z) form can be efficiently separated from the (E) form and recovered.

The alcohol used in step (B) may be a linear alcohol or branched alcohol. The aforementioned alcohol is preferably a lower alcohol having 1 to 6 carbon atoms and more preferably a lower alcohol having 1 to 4 carbon atoms. Specific examples thereof include methanol, ethanol, n-propanol, isopropanol (2-propanol), n-butanol, 2-butanol, 2-methyl-1-propanol and 2-methyl-2-propanol. Among these, methanol, ethanol, n-propanol and isopropanol are preferable, and isopropanol is more preferable.

Although there are no particular limitations on the amount of alcohol added to the aqueous solution of the compound represented by general formula (I) provided it is an amount that allows crystallization of the (Z) form, it is preferably roughly an amount equal to 1 to 100 times the amount of the aqueous solution and more preferably roughly an amount equal to 2 to 30 times the amount of the aqueous solution. The alcohol may be added to the aforementioned aqueous solution all at once or may be added by dividing among a plurality of additions.

The crystallization temperature in step (B) is only required to be that which is equal to or lower than the boiling point of the alcohol, and the crystallization reaction can be carried out a temperature of, for example, 20° C. to 80° C., preferably 30° C. to 70° C. and more preferably 40° C. to 65° C. In addition, stirring may be carried out during crystallization. Subsequently, the aqueous solution may be cooled to about 0° C. to 10° C. as necessary and allowed to stand for about 30 minutes to 2 hours.

Precipitated crystals of the (Z) form contain two molecules of water per molecule thereof in the form of crystalline water. These crystals can be recovered by solid-liquid separation treatment. The recovered crystals may be washed with an aqueous alcohol and the like followed by drying as necessary.

<Method for Producing (Z) Form of Compound Represented by General Formula (I)>

The compound represented by general formula (I) undergoes an isomerization reaction when irradiated with light in the same manner as the tetrazolyloxime derivative represented by general formula (II), and ultimately the abundance ratio between the (E) form and the (Z) form (the ratio at which each isomer is present based on the total amount of the (E) form and the (Z) form) reaches a state of equilibrium. Consequently, in the case the abundance ratio of the (Z) form is lower than the abundance ratio at equilibrium in a solution in which the compound represented by general formula (I) has been dissolved in a suitable solvent, the content of the (Z) form can be further increased due to the occurrence of a photoisomerization reaction in the aforementioned solution. In particular, the compound represented by general formula (I) demonstrates a faster photoisomerization rate than the tetrazolyloxime derivative represented by general formula (II), and equilibrium is reached in a shorter amount of time. Consequently, the compound represented by general formula (I) enables the amount of the (Z) form to be increased by the photoisomerization reaction in a shorter amount of time than the tetrazolyloxime derivative represented by general formula (II).

More specifically, the (Z) form can be produced by a step (C) for isomerizing the (E) form to the (Z) form by irradiating a solution containing the (E) form of the compound represented by general formula (I) with light.

Although there are no particular limitations on the content of the (Z) form of the compound represented by general formula (I) in the solution irradiated with light in step (C), it is preferably lower than the abundance ratio of the (Z) form at the final state of equilibrium reached due to the photoisomerization reaction. Namely, the abundance ratio of the (Z) form of the compound represented by general formula (I) in the solution irradiated with light in step (C) is preferably 10% or less, more preferably 5% or less and even more preferably 1% or less.

There are no particular limitations on the solvent of the solution irradiated with light in step (C) provided it is able to dissolve the compound represented by general formula (I) and not readily absorb the radiated light, and may be water or an organic solvent. In step (C), the solvent is preferably water since it exhibits favorable solubility with respect to the compound represented by general formula (I) and has high light transmittance. The aqueous solution of the compound represented by general formula (I) may also contain other components in addition to water and the compound represented by general formula (I) provided they do not impair the photoisomerization reaction.

There are no particular limitations on the light radiated in step (C) provided it is able to impart light energy sufficient for isomerizing the compound represented by general formula (I) from the (E) form to the (Z) form. The light radiated in step (C) is preferably ultraviolet light, is more preferably light having a wavelength of 185 nm to 400 nm, and even more preferably light having a wavelength of 300 nm to 400 nm.

The time during which light is radiated in step (C) is required to be an amount of time that results in an exposure dose that allows the isomerization reaction of the compound represented by general formula (I) to proceed in the solution, and although radiation of light may be discontinued before the aforementioned solution has reached equilibrium, the amount of time is preferably that which results in an exposure dose that is sufficient for reaching equilibrium. Normally, the abundance ratio of the (Z) form is greater than that of the (E) form at equilibrium. In other words, as a result of reaching equilibrium, the content of the (Z) form in the solution can be increased to the maximum amount that can be expected to be achieved by the photoisomerization reaction. Since the isomerization reaction rate of the compound represented by general formula (I) is fast, for example, equilibrium can be reached by irradiating with light of a wavelength of 365 nm for 15 minutes to 60 minutes.

In addition, the (Z) form of the compound represented by general formula (I) can be obtained in a large amount even more efficiently by combining the aforementioned steps (B) and (C).

For example, the solution irradiated with light in the aforementioned step (C) is set to an aqueous solution containing the (E) form of the compound represented by general formula (I) and the (E) form is isomerized to the (Z) form by irradiating the aforementioned solution with light (step (C')), followed by precipitating crystals of the (Z) form of the compound represented by general formula (I) by adding an alcohol to the aforementioned solution (step (B')). According to the aforementioned method, the (Z) form, for which the amount thereof has been increased by a photoisomerization reaction, can be separated from the (E) form and precipitated as crystals by alcohol crystallization.

In addition, following the aforementioned step (B), a trace amount of the (Z) form and a larger amount of the (E) form are contained in the remaining mother liquor from which crystals of the (Z) form have been recovered by solid-liquid separation treatment. Therefore, the aforementioned mother liquor is set to a solution that is irradiated with light in the aforementioned step (C) followed by irradiating with light to isomerize the (E) form in the aforementioned mother liquor to the (Z) form. Following the photoisomerization reaction, the newly obtained (Z) form can be precipitated as crystals by concentrating the aforementioned mother liquor or repeating addition of alcohol.

As a result of carrying out this series of steps, a highly pure (Z) form, in which the contaminating amount of the (E) form is extremely low, can be recovered rapidly and in a large amount from a mixture of the (Z) form and the (E) form obtained by a synthesis reaction such as that of step (A).

<Method for Producing Tetrazolyloxime Derivative Represented by General Formula (IV)>

The compound represented by general formula (I) is useful as an intermediate for producing a plant disease control agent and the like.

For example, a tetrazolyloxime derivative represented by general formula (IV) can be obtained by reacting the compound represented by general formula (I) with a halide represented by general formula (III) (step (D1)).

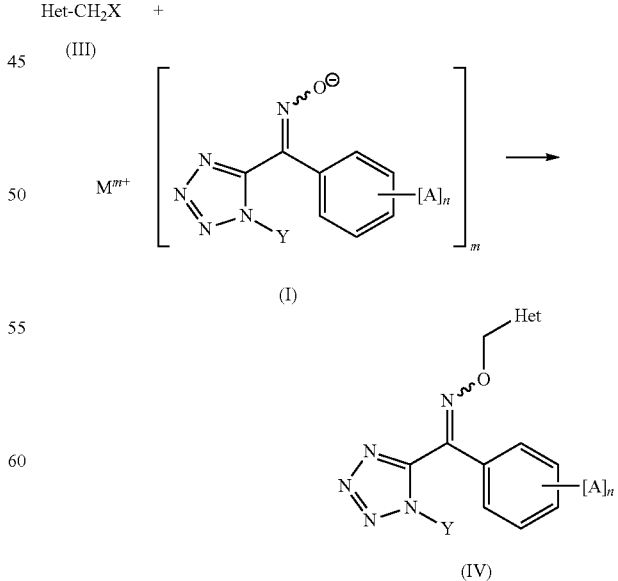

In general formula (III), Het represents a substituted pyridyl group or substituted thiazolyl group. Substituents in the substituted pyridyl group or substituted thiazolyl group represented by Het can be substituted with chemically acceptable groups by a known chemical reaction.

In general formula (III), X represents a halogen atom. Examples of halogen atoms include a fluorine atom, chlorine atom, bromine atom and iodine atom.

In general formula (IV), Het, X, A, n and Y are respectively the same as in general formula (III) and general formula (I).

Examples of the halide represented by general formula (III) include halogenated picoline derivatives represented by general formula (VI) (see, for example, Patent Document 3):

[Chemical Formula 11]

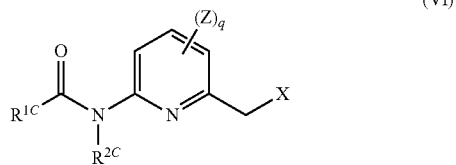

(VI)

(wherein, $R^{1C}$ represents an unsubstituted or substituted alkyl group or unsubstituted or substituted alkoxy group, $R^{2C}$ represents a hydrogen atom, unsubstituted or substituted alkoxycarbonyl group or unsubstituted or substituted acyl group, X represents a halogen atom, Z represents a halogen atom, cyano group, nitro group, hydroxyl group, thiol group, formyl group, carboxyl group, unsubstituted or substituted amino group, unsubstituted or substituted alkyl group, unsubstituted or substituted alkenyl group, unsubstituted or substituted alkynyl group, unsubstituted or substituted aryl group, unsubstituted or substituted heterocyclic group, $OR^3$, $S(O)_pR^3$, $COR^3$ or $CO_2R^3$ (wherein, $R^3$ represents an unsubstituted or substituted amino group, unsubstituted or substituted alkyl group, unsubstituted or substituted alkenyl group, unsubstituted or substituted alkynyl group, unsubstituted or substituted aryl group or unsubstituted or substituted heterocyclic group, and p indicates the number of oxygen atoms shown in parentheses and is an integer of 0 to 2), and q indicates the number of substituents Z and is an integer of 0 to 3, and a plurality of Z may be mutually the same or different when q is 2 or more).

In general formula (VI), $R^{1C}$ represents an unsubstituted or substituted alkyl group or unsubstituted or substituted alkoxy group. There are no particular limitations on the substituents in $R^{1C}$ provided they are inert in a reaction with the compound represented by general formula (I).

The alkyl group in $R^{1C}$ may be linear, branched or cyclic. In addition, the number of carbon atoms of the aforementioned alkyl group is preferably 1 to 6.

Examples of unsubstituted alkyl groups include a methyl group, ethyl group, n-propyl group, i-propyl group, n-butyl group, i-butyl group, s-butyl group, t-butyl group, n-pentyl group, n-octyl group, cyclopropyl group, cyclobutyl group, cyclopentyl group, cyclohexyl group, cycloheptyl group, 2,2-dimethylcyclopropyl group and menthyl group.

Examples of substituted alkyl groups include a chloromethyl group, fluoromethyl group, trifluoromethyl group, methoxymethyl group, ethoxymethyl group, methoxyethyl group, methoxypropyl group, ethoxybutyl group, methoxybutyl group, methoxyhexyl group, propoxyoctyl group, 2-methoxy-1,1-dimethylethyl group, 1-ethoxy-1-methylethyl group, carbomethoxymethyl group, 1-carboethoxy-2,2-dimethyl-3-cyclopropyl group, hydroxymethyl group, hydroxyethyl group and 1-hydroxypropyl group. The substituted alkyl group is preferably a haloalkyl group.

The alkoxy group in $R^{1C}$ may be linear, branched or cyclic. The aforementioned alkoxy group preferably has 1 to 6 carbon atoms.

Examples of unsubstituted alkoxy groups include a methoxy group, ethoxy group, n-propoxy group, i-propoxy group, n-butoxy group, i-butoxy group, s-butoxy group, t-butoxy group, n-pentyloxy group, n-hexyloxy group, n-decyloxy group, cyclopropyloxy group, cyclobutyloxy group, cyclopentyloxy group, cyclohexyloxy group and menthyloxy group.

Examples of substituted alkoxy groups include a chloromethoxy group, fluoromethoxy group, trifluoromethoxy group, methoxymethoxy group, ethoxymethoxy group, methoxyethoxy group, 3-ethoxypropoxy group, 2-ethoxybutoxy group, 4-butoxybutoxy group, 1-butoxypentoxy group, fluoromethoxymethoxy group, dichloromethoxymethoxy group, 1,2-dibromo-3-methoxypropoxy group and 3-isopropoxy-2-methylpropoxy group.

In general formula (VI), $R^{2C}$ represents a hydrogen atom, unsubstituted or substituted alkoxycarbonyl group or unsubstituted or substituted acyl group.

Examples of unsubstituted alkoxycarbonyl groups in $R^{2C}$ include a methoxycarbonyl group, ethoxycarbonyl group, i-propoxycarbonyl group, n-propoxycarbonyl group, n-butoxycarbonyl group, i-butoxycarbonyl group, s-butoxycarbonyl group and t-butoxycarbonyl group.

Examples of substituted alkoxycarbonyl groups in $R^{2C}$ include a cyanomethoxycarbonyl group, 1-cyanoethoxycarbonyl group, 2-cyanoethoxycarbonyl group, nitromethoxycarbonyl group, chloromethoxycarbonyl group, fluoromethoxycarbonyl group, difluoromethoxycarbonyl group, trifluoromethoxycarbonyl group, 2-fluoroethoxycarbonyl group, 2,2,2-trifluoroethoxycarbonyl group, methoxymethoxycarbonyl group, ethoxymethoxycarbonyl group, 1-methoxyethoxycarbonyl group, 2-methoxyethoxycarbonyl group and 2-chloroethoxymethoxycarbonyl group.

An acyl group in $R^{2C}$ is a group in which a hydrogen atom, alkyl group, alkenyl group, alkynyl group, aryl group or heterocyclic group is bound to a carbonyl group.

Examples of unsubstituted aryl groups include alkylcarbonyl groups such as a formyl group, acetyl group, propionyl group, n-propylcarbonyl group, n-butylcarbonyl group, octanoyl group, i-propylcarbonyl group, i-butylcarbonyl group, pivaloyl group or isovaleryl group, alkenylcarbonyl groups such as a acryloyl group or methacryloyl group, alkynylcarbonyl groups such as a propioloyl group, arylcarbonyl groups such as a benzoyl group, and heterocyclic carbonyl groups such as a 2-pyridylcarbonyl group or thienylcarbonyl group.

Examples of substituted aryl groups in $R^{2C}$ include a fluoroacetyl group, chloroacetyl group, nitroacetyl group, cyanoacetyl group, methoxyacetyl group, dibromoacetyl group, trifluoroacetyl group, trichloroacetyl group, tribromoacetyl group, 3,3,3-trifluoropropionyl group, 3,3,3-trichloropropionyl group, 2,2,3,3,3-pentafluoropropionyl group and 4-chlorobenzoyl group.

Among these, $R^{2C}$ in general formula (VI) is preferably a hydrogen atom, unsubstituted benzoyl group or substituted benzoyl group. Examples of substituted benzoyl groups include a 2,6-dimethoxybenzoyl group, 3,5-nitrobenzoyl group, 2,4,6-trichlorobenzoyl group and 4-chlorobenzoyl group.

In general formula (VI), X represents a halogen atom. Examples of halogen atoms include a fluorine atom, chlorine atom, bromine atom and iodine atom. Among these, a chlorine atom or bromine atom is preferable.

In general formula (VI), Z represents a halogen atom, cyano group, nitro group, hydroxyl group, thiol group, formyl group, carboxyl group, unsubstituted or substituted amino group, unsubstituted or substituted alkyl group, unsubstituted or substituted alkenyl group, unsubstituted or substituted alkynyl group, unsubstituted or substituted aryl group, unsubstituted or substituted heterocyclic group, $OR^3$, $S(O)_pR^3$, $COR^3$ or $CO_2R^3$.

Examples of halogen atoms in Z are the same as examples of halogen atoms in X.

An unsubstituted amino group in Z is a group having an $NH_2$-structure. Examples of substituted amino groups include a methylamino group, dimethylamino group, methylethylamino group, diethylamino group, t-butoxycarbonylmethylamino group, t-butoxycarbonylamino group, acetylmethylamino group, acetylethylamino group and benzoylmethylamino group.

Examples of unsubstituted or substituted alkyl groups in Z are the same as examples of unsubstituted or substituted alkyl groups in the aforementioned $R^{1C}$.

The unsubstituted or substituted alkenyl group in Z is preferably that having 2 to 8 carbon atoms.

Examples of unsubstituted alkenyl groups include a vinyl group, 1-propenyl group, 2-propenyl group, 1-butenyl group, 2-butenyl group, 3-butenyl group, 1-methyl-2-propenyl group, 2-methyl-2-propenyl group, 1-pentenyl group, 2-pentenyl group, 3-pentenyl group, 4-pentenyl group, 1-methyl-2-butenyl group, 2-methyl-2-butenyl group, 1-hexenyl group, 2-hexenyl group, 3-hexenyl group, 4-hexenyl group and 5-hexenyl group.

Examples of substituted alkenyl groups include a 2-chloroethenyl group, 2-fluoroethenyl group, 3,3,3-trifluoro-1-pentenyl group, 1,2,2-trifluoroethenyl group, 2,3,3-trifluoro-2-propenyl group, 2,3,3-triiodo-2-propenyl group and 2-methoxyethenyl group.

The unsubstituted or substituted alkynyl group in Z is preferably that having 2 to 8 carbon atoms.

Examples of unsubstituted alkynyl groups include an ethynyl group, 1-propynyl group, 2-propynyl group, 1-butynyl group, 2-butynyl group, 3-butynyl group, 1-methyl-2-propynyl group, 2-methyl-3-butynyl group, 1-pentynyl group, 2-pentynyl group, 3-pentynyl group, 4-pentynyl group, 1-methyl-2-butynyl group, 2-methyl-3-pentynyl group, 1-hexynyl group and 1,1-dimethyl-2-butynyl group.

Examples of substituted alkynyl groups include a 2-chloroethynyl group, 2-fluoroethynyl group, 3-fluoro-1-propynyl group, 3,3,3-trifluoro-1-propynyl group, 3-fluoro-2-propynyl group and 3-iodo-2-propynyl group.

An unsubstituted or substituted aryl group in Z is a monocyclic or polycyclic aryl group. The polycyclic aryl group is such that, provided at least one of the rings is an aromatic ring, the remaining rings may be saturated aliphatic rings, unsaturated aliphatic rings or aromatic rings.

Examples of unsubstituted aryl groups include a phenyl group, 1-naphthyl group, 2-naphthyl group, azulenyl group, indenyl group, indanyl group or tetralinyl group.

Examples of substituted aryl groups include a 6-methylphenyl group, 4-methylphenyl group, 4-fluorophenyl group, 4-chlorophenyl group, 2,4-dichlorophenyl group, 3,4-dichlorophenyl group, 3,5-dichlorophenyl group, 2,6-difluorophenyl group, 4-trifluoromethylphenyl group, 4-methoxyphenyl group, 3,4-dimethoxyphenyl group, 3,4-methylenedioxyphenyl group, 3-phenoxyphenyl group, 4-trifluoromethoxyphenyl group and 4-methoxy-1-naphthyl group.

Examples of unsubstituted heterocyclic groups in Z include unsaturated five-membered heterocyclic groups such as a furan-2-yl group, furan-3-yl group, thiophen-2-yl group, thiophen-3-yl group, pyrrol-2-yl group, pyrrol-3-yl group, oxazol-2-yl group, oxazol-4-yl group, oxazol-5-yl group, thiazol-2-yl group, thiazol-4-yl group, thiazol-5-yl group, isoxazol-3-yl group, isoxazol-4-yl group, isoxazol-5-yl group, isothiazol-3-yl group, isothiazol-4-yl group, isothiazol-5-yl group, imidazol-2-yl group, imidazol-4-yl group, imidazol-5-yl group, pyrazol-3-yl group, pyrazol-4-yl group, pyrazol-5-yl group, 1,3,4-oxadiazol-2-yl group, 1,3,4-thiadiazol-2-yl group, 1,2,3-triazol-4-yl group, 1,2,4-triazol-3-yl group or 1,2,4-triazol-5-yl group; unsaturated six-membered heterocyclic groups such as a pyridin-2-yl group, pyridin-3-yl group, pyridin-4-yl group, 5-chloro-3-pyridyl group, 3-trifluoromethyl-2-pyridyl group, pyridazin-3-yl group, pyridazin-4-yl group, pyrazin-2-yl group, pyrimidin-5-yl group, 1,3,5-triazin-2-yl group or 1,2,4-triazin-3-yl group; and, saturated or partially unsaturated heterocyclic groups such as a tetrahydrofuran-2-yl group, tetrahydropyran-4-yl group, piperidin-3-yl group, pyrrolidin-2-yl group, morpholino group, piperidino group, piperazino group, N-methylpiperazino group, azylidino group, azetidino group, pyrrolidino group or oxazolin-2-yl group.

Examples of substituted heterocyclic groups include a 3-trifluoromethylpyridin-2-yl group, 4-trifluoromethoxy-2-pyridyl group, 3-methyl-1-pyrazolyl group, 4-trifluoromethyl-1-imidazolyl group and 3,4-difluoropyrrolidino group.

$R^3$ in $OR^3$, $S(O)_pR^3$, $COR^3$ or $CO_2R^3$ representing Z represents an unsubstituted or substituted amino group, unsubstituted or substituted alkyl group, unsubstituted or substituted alkenyl group, unsubstituted or substituted alkynyl group, unsubstituted or substituted aryl group or unsubstituted or substituted heterocyclic group. p indicates the number of oxygen atoms shown in parentheses and is an integer of 0 to 2.

Examples of the unsubstituted or substituted amino group, unsubstituted or substituted alkyl group, unsubstituted or substituted alkenyl group, unsubstituted or substituted alkynyl group, unsubstituted or substituted aryl group and unsubstituted or substituted heterocyclic group in $R^3$ are the same as examples indicated in the aforementioned explanations of $R^{1C}$ and Z.

Specific examples of $OR^3$ include a methoxy group, ethoxy group, n-propoxy group, i-propoxy group, n-butoxy group, s-butoxy group, i-butoxy group, t-butoxy group, methoxymethoxy group, ethoxymethoxy group, methoxyethoxy group, ethoxyethoxy group, vinyloxy group, 1-propenyloxy group, 2-propenyloxy group, ethynyloxy group, 1-propynyloxy group, 2-propynyloxy group, aminooxy group, methylaminooxy group, diethylaminooxy group, methoxycarbonylaminooxy group, phenoxy group, trichloromethoxy group, trifluoromethoxy group, difluoromethoxy group, 2,2,2-trifluoroethoxy group, pentafluoroethoxy group and 2-fluoroethoxy group.

Specific examples of $S(O)_pR^3$ include a dimethylaminothio group, chloromethylthio group, 3-butenylthio group, ethynylthio group, 3-methylphenylthio group, methylsulfinyl group, ethylsulfinyl group, 1-butenylsulfinyl group, 1-hexynylsulfinyl group, 2,3-dimethylphenylsulfinyl group, methylsulfonyl group, dimethylaminosulfonyl group, N-ethyl-N-methylaminosulfonyl group, n-hexylsulfonyl group, 2-methyl-2-butenylsulfonyl group, 2-propynylsulfonyl group, 2-naphthylsulfonyl group, phenylsulfonyl group, 2-nitrophenylsulfonyl group and p-tolylsulfonyl group.

Specific examples of $COR^3$ include an acetyl group, benzoyl group, propanoyl group, i-propylcarbonyl group, t-butylcarbonyl group, cyclopropylcarbonyl group, cyclobutylcarbonyl group, cyclopentylcarbonyl group, vinylcarbonyl group, 1-propenylcarbonyl group, 2-propenylcarbonyl group, i-propenylcarbonyl group, 1-propynylcarbonyl group, 2-propynylcarbonyl group, 3-butenylcarbonyl group, methylaminocarbonyl group, dimethylaminocarbonyl group, N-methyl-N-ethylaminocarbonyl group, aziridinocarbonyl group, azetidinocarbonyl group, pyrrolidinocarbonyl group, piperidinocarbonyl group, morpholinocarbonyl group, piperazinocarbonyl group and N-methylpiperazinocarbonyl group.

Specific examples of $CO_2R^3$ include a methoxycarbonyl group, trifluoromethoxycarbonyl group, 1-pentenyloxycarbonyl group, 2-propynyloxycarbonyl group and phenoxycarbonyl group.

Among these, Z in general formula (VI) is preferably a halogen atom, unsubstituted or substituted amino group, unsubstituted alkyl group, $OR^3$ or $SR^3$, and more preferably an unsubstituted or substituted amino group, unsubstituted alkyl group, $OR^3$ or $SR^3$. The unsubstituted or substituted amino group in Z is preferably an unsubstituted amino group or dialkylamino group, the unsubstituted alkyl group is preferably that having 1 to 4 carbon atoms, $OR^3$ is preferably an alkoxy group having 1 to 4 carbon atoms, and $SR^3$ is preferably an alkylthio group having 1 to 4 carbon atoms.

In general formula (VI), q indicates the number of substituents Z and is an integer of 0 to 3. A plurality of Z may be mutually the same or different when q is 2 or more, and q is particularly preferably 0.

The halogenated picoline derivative represented by general formula (VI) can be obtained by reacting a halogenating agent with a 2-amino-6-methylpyridine derivative having the corresponding structure.

The reaction in step (D1) may also be carried out in the presence of a base. Examples of bases used in this reaction include inorganic bases such as sodium hydroxide, potassium hydroxide, sodium hydride, sodium carbonate or potassium carbonate, and organic bases such as triethylamine, 4-(dimethylamino)pyridine, pyridine, 1,8-diazabicyclo[5.4.0]undecene-7 or 1,5-diazabicyclo[4.3.0]nonene-5. One type of these bases can be used alone or two or more types can be used in combination. Among these, alkaline metal hydroxides such as sodium hydroxide or potassium hydroxide are used preferably.

The amount of base used is normally 0.01 moles to 100 moles, and preferably 0.1 moles to 5 moles, based on 1 mole of the compound represented by general formula (I).

This reaction can be carried out in the presence or absence of solvent.

There are no particular limitations on the solvent used provided it is a solvent that is inert in the present reaction. Examples of solvents include hydrocarbon-based solvents such as pentane, hexane, heptane, benzene, toluene or xylene, halogen-based solvents such as dichloromethane, chloroform or carbon tetrachloride, nitrile-based solvents such as acetonitrile or propionitrile, ether-based solvents such as diethyl ether, dioxane or tetrahydrofuran, amide-based solvents such as N,N-dimethylformamide, N,N-dimethylacetamide or N-methylpyrrolidone, sulfoxide-based solvents such as dimethylsulfoxide, water and mixed solvents thereof.

There are no particular limitations on the procedure and so forth of the reaction between the halogenated picoline derivative represented by general formula (VI) and the compound represented by general formula (I). For example, the compound represented by general formula (I) may be added to an organic solvent solution containing the halogenated picoline derivative represented by general formula (VI) and allowed to react.

Although the temperature from start to finish of the reaction of step (D1) may be held constant or allowed to vary, it is normally a temperature within the range of −70° C. to +200° C. and preferably within the range of −20° C. to +100° C. Although varying according to such factors as the reaction scale, the reaction time is normally 30 minutes to 24 hours.

In the case of using a compound in which $R^{2C}$ is not a hydrogen atom for the halogenated picoline derivative represented by general formula (VI), a tetrazolyloxime derivative in which $R^{2C}$ in general formula (IV) is a hydrogen atom can be obtained by allowing a base to act on the tetrazolyloxime derivative represented by general formula (IV) obtained after step (D1) (step (D2)).

Furthermore, base may be reacted with the reaction product, namely the tetrazolyloxime derivative represented by general formula (IV), without carrying out a purification procedure on the reaction liquid obtained by going through the aforementioned step (D1), or a purification procedure may be carried out on the reaction liquid obtained by going through step (D1) followed by isolating the aforementioned reaction product and allowing base to act thereon. Examples of purification procedures include distillation, recrystallization and column chromatography.

There are no particular limitations on the base used in step (D2) provided it is able to cause elimination of $R^{2C}$ in the tetrazolyloxime derivative represented by general formula (IV). Examples of base include alkaline metal hydroxides such as sodium hydroxide or potassium hydroxide, alkaline earth metal hydroxides such as magnesium hydroxide or calcium hydroxide, carbonates such as sodium carbonate, potassium carbonate, magnesium carbonate or calcium carbonate, hydrides such as sodium hydride or calcium hydride, metal alkoxides such as sodium methoxide, sodium ethoxide or magnesium methoxide, and organic bases such as triethylamine, triisopropylethylamine, pyridine, N,N-dimethylaminopyridine, 1,4-diazabicyclo[2.2.2]octane, 4-(dimethylamino)pyridine, 1,8-diazabicyclo[5.4.0]undec-7-end or 1,5-diazabicyclo[4.3.0]non-5-ene. One type of these bases can be used alone or two or more types can be used in combination.

The amount of base used in step (D2) is normally 0.01 moles to 100 moles, and preferably 0.1 moles to 5 moles, based on 1 mole of the tetrazolyloxime derivative represented by general formula (IV).

Furthermore, in the case of carrying out the reaction of step (D1) in the presence of base and using the reaction liquid obtained in step (D1) directly in step (D2) without removing the base from the reaction liquid obtained in step (D1), the amount of base added in step (D2) can be adjusted in consideration of the amount of base used in step (D1).

The reaction of step (D2) can be carried out in the presence or absence of solvent. There are no particular limitations on the solvent used provided it is inert in the present reaction. Specific examples thereof are the same as those listed as examples of solvents in the explanation of step (D1). If the solvent used in step (D2) is the same as the solvent used in step (D1), it is not necessary to replace the solvent when proceeding from step (D1) to step (D2), which is advantageous in terms of production cost.

There are no particular limitations on the procedure and so forth used to allow the base to act on the reaction product in step (D1). For example, the reaction may be carried out by adding base to the reaction product of step (D1), namely the organic solvent solution containing the tetrazolyloxime derivative represented by general formula (IV).

Although the temperature from start to finish of the reaction of step (D2) may be held constant or allowed to vary, it is normally a temperature within the range of −0° C. to the boiling point of the solvent and preferably within the range of 10° C. to 60° C. Although varying according to such factors as the concentration of base or reaction scale, the reaction time is normally 5 minutes to 24 hours.

In addition, a salt of the tetrazolyloxime derivative represented by general formula (IV) can be produced by allowing an acid to act on the aforementioned tetrazolyloxime derivative in accordance with routine methods. There are no particular limitations on the salt of the tetrazolyloxime derivative represented by general formula (IV) provided it is an agrihorticulturally acceptable salt. Examples thereof include salts of inorganic acids such as hydrochlorides, nitrates, sulfates or phosphates, and salts of organic acids such as acetates, lactates, propionates or benzoates.

The target tetrazolyloxime derivative represented by general formula (IV) and a salt thereof can be isolated by carrying out an ordinary post-treatment procedure following completion of any of the reactions. In addition, if purification of a product is required, a known, commonly used purification means such as distillation, recrystallization or column chromatography can be employed. The structure of the target product can be identified and confirmed by measurement of $^1$H-NMR spectrum, IR spectrum or mass spectrum, or by elementary analysis and the like.

The tetrazolyloxime derivative represented by general formula (IV), or salt thereof, obtained in this manner is preferable for use as an active ingredient of a bactericide and the like. The aforementioned bactericide can be used as an agricultural chemical preparation for assisting the growth of agricultural and horticultural crops, as an agent for preventing adherence of crustaceans and shellfish, or as an antibacterial agent or anti-mold agent for walls, bathtubs, shoes or clothing.

EXAMPLES

Although the following provides a more detailed explanation of the present invention through examples thereof, the present invention is not limited to these examples.

Example 1

5 g of pure water (0.1 L/mol relative to TZ) and 90 mL of methanol (0.9 L/mol) were added to a 300 mL four-mouth flask. (1-methyl)-1H-tetrazol-5-yl)(phenyl)methanone (TZ) (0.05 mol) and 6.2 g of HAS (hydroxylamine sulfate) (1.50 mol %/TZ) were added thereto followed by reacting for 20 hours at 55° C. to 60° C.

After confirming that the reaction had ended by HPLC, the methanol and water were concentrated under reduced pressure to form a slurry followed by adding 50 ml (1 L/mol) of pure water thereto and carrying out crystallization at 5° C. The precipitated crystals were filtered out and washed twice with 25 mL of pure water followed by drying to obtain 9.14 g of (1-methyl-1H-tetrazol-5-yl)(phenyl)methanoneoxime (TZOX) (yield: 90 mol %/TZ). The abundance ratio between the (E) form and the (Z) form of the resulting TZOX was such that (E) form:(Z) form=8:92.

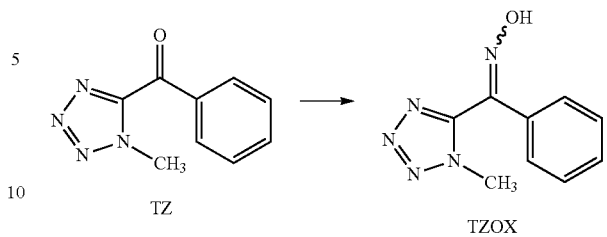

3.3 g of pure water (65 g/mol with respect to TZOX) and 8.57 g of 28% by weight aqueous sodium hydroxide solution (120 mol % with respect to TZOX) were added to a 300 mL four-mouth flask. 10.16 g (0.05 mol, E:Z=8:92) of the previously synthesized TZOX were added while heating this liquid to 55° C. to 60° C. After reacting for 0.5 hours while in this state, 100 mL (2 L/mol) of isopropyl alcohol (IPA) were added. Subsequently, after reacting for 1 hour at 50±5° C., the liquid was cooled to 5° C. or lower and allowed to crystallize for 1 hour.

After filtering out the precipitated TZOX-Na salt, the crystals were washed with 50 mL of a solution of IPA/H2O=90:10 while cooling followed by drying.

When the dried TZOX-Na crystals were weighed, they were found to weigh 11.8 g (purity: 77% by weight as TZOX). In addition, the abundance ratio of the (E) form to the (Z) form was 0.5:99.5, and the recovery rate of the (Z) form was 95% or higher. In addition, the aforementioned TZOX-Na salt was a compound that has two molecules of crystallized water.

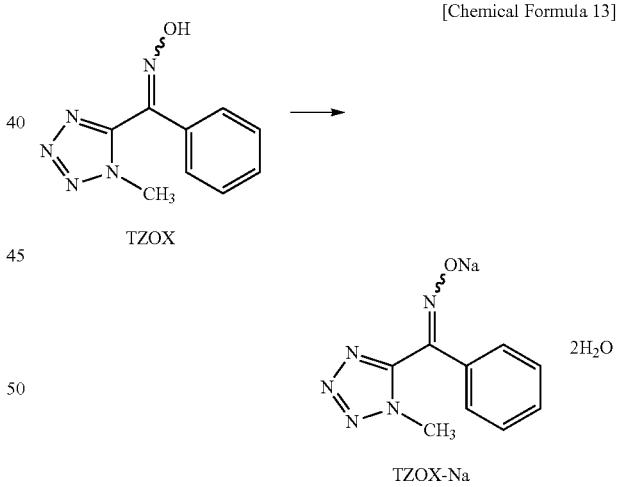

Example 2

20 g (200 g/mol relative to TZOX) of pure water and 7.6 g (120 mol % relative to TZOX) of crystalline potassium hydroxide were added to a 300 mL four-mouth flask and dissolved. 20.3 g (0.10 mol, E:Z=6:94) of the previously synthesized TZOX were added while heating this liquid to 55° C. to 60° C. After reacting for 0.5 hours while in this state, 200 mL (2 L/mol) of IPA were added. Subsequently, after reacting for 1 hour at 50±5° C., the liquid was cooled to 5° C. or lower and allowed to crystallize for 1 hour.

After filtering out the precipitated TZOX-K salt, the crystals were washed with 50 mL of a solution of IPA/H2O=90:10 while cooling followed by drying.

When the dried TZOX-K crystals were weighed, they were found to weigh 20.1 g (purity: 74% by weight as TZOX). In addition, the abundance ratio between the (E) form and the (Z) form was 99.5:0.5, and the recovery rate of the (Z) form was 77%. In addition, the aforementioned TZOX-K salt was a compound that has two molecules of crystallized water.

[Chemical Formula 14]

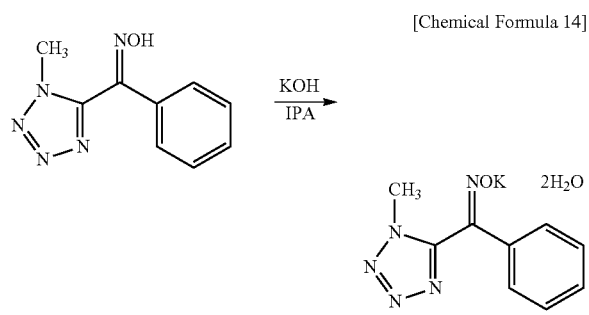

Since the resulting TZOX-K.2H$_2$O is a salt that contains two molecules of water, it can be handled more safely in comparison with the conventional free form of TZOX that is associated with the risk of dust explosion.

Example 3

25 g (250 g/mol relative to TZOX) of pure water and 5.0 g (120 mol % relative to TZOX) of crystalline lithium hydroxide were added to a 300 mL four-mouth flask and dissolved. 20.3 g (0.10 mol, E:Z=6:94) of the previously synthesized TZOX were added while heating this liquid to 55° C. to 60° C. After reacting for 0.5 hours while in this state, 200 mL (2 L/mol) of IPA were added. Subsequently, after reacting for 1 hour at 50±5° C., the liquid was cooled to 5° C. or lower and allowed to crystallize for 3 hours to 5 hours.

After filtering out the precipitated TZOX-Li salt, the crystals were washed with 50 mL of a solution of IPA/H2O=90:10 while cooling followed by drying.

When the dried TZOX-Li crystals were weighed, they were found to weigh 20.1 g (purity: 83% by weight as TZOX). In addition, the abundance ratio between the (E) form and the (Z) form was 99.5:0.5, and the recovery rate of the (Z) form was 90%. In addition, the aforementioned TZOX-Li salt was a compound that has two molecules of crystallized water.

[Chemical Formula 15]

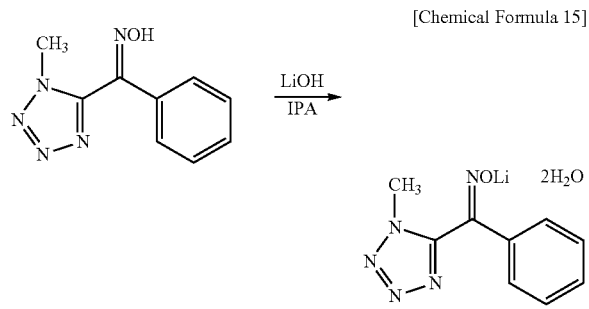

Since the resulting TZOX-Li.2H$_2$O is a salt that contains two molecules of water, it can be handled more safely in comparison with the conventional free form of TZOX that is associated with the risk of dust explosion. In addition, results were also obtained indicating that water is released at a lower temperature in the case of this Li salt alone in comparison with the K salt or Na salt.

Example 4

In the filtrate obtained following crystallization in Example 1, the (E) form and (Z) form were contained at an abundance ratio of (E) form:(Z) form=8:2 and TZOX-Na salt concentration of 1% by weight.

The aforementioned filtrate was irradiated with light (wavelength: 365 nm) for 15 minutes to 30 minutes using a high-pressure mercury lamp. When the abundance ratio of the (E) form and (Z) form in the filtrate following irradiation with light was investigated, it was found to be such that (E) form:(Z) form=35:65. In other words, the TZOX-Na salt was determined to be isomerized by irradiation with light in an extremely short period of time, namely that the rate of the isomerization reaction is fast. In addition, the filtrate (water/IPA) was concentrated following irradiation with light and the precipitated TZOX-Na salt was recovered by filtration. The recovered TZOX-Na salt contained the (Z) form at about 50% of the total amount (mol %) of the (E) form and the (Z) form in the filtrate after crystallization (filtrate prior to the start of irradiating with light). Moreover, roughly 70% of the (Z) form was ultimately able to be recovered as a result of similarly repeating concentration and filtration on the resulting refiltered filtrate.

Example 5

The reaction rates of the isomerization reaction were compared for the TZOX and TZOX-Na salt synthesized in Example 1.

More specifically, 1% by weight aqueous solutions of each were prepared followed by irradiating these aqueous solutions with light (wavelength: 365 nm) for 3 hours using a high-pressure mercury lamp. A portion of the aqueous solutions were sampled prior to the start of irradiation with light (irradiation time: 0 hours) and at 1, 2 and 3 hours after the start of irradiation with light followed by an investigation of the abundance ratios of the (E) form and (Z) form. The results are shown in Table 1. Although the abundance ratio of the (Z) form in the case of TZOX-Na prior to irradiation with light was only 0.33%, it increased to 34% after 1 hour had elapsed since the start of irradiation and remained essentially unchanged after that point. In other words, it was determined that the TZOX-Na salt reaches equilibrium as a result of being irradiated with light for 1 hour, and that the isomerization rate thereof is extremely fast. In contrast, in the case of TZOX, the abundance ratio of the (Z) form only finally reached 35% after 3 hours had elapsed since the start of irradiation, and it was determined that at least 2 hours are required to reach equilibrium.

TABLE 1

| Light Irradiation Time | Abundance Ratio (%) | | | |
| --- | --- | --- | --- | --- |
| | TZOX | | TZOX-Na | |
| | (E) form | (Z) form | (E) form | (Z) form |
| 0 hours | 99.52 | 0.45 | 99.43 | 0.33 |
| 1 hour | 83.99 | 13.7 | 64.0 | 34.0 |
| 2 hours | 70.39 | 28.13 | 63.0 | 33.9 |
| 3 hours | 62.8 | 35.3 | 66.6 | 32.3 |

INDUSTRIAL APPLICABILITY

The compound of the present invention is useful as a synthesis intermediate of a tetrazolyloxime derivative that is useful as an active ingredient of an agricultural chemical and the like. Consequently, use of the compound of the present invention makes it possible to produce a tetrazolyloxime derivative, and particularly the (Z) form thereof which is an stereoisomer having higher pharmacological efficacy, with both high selectivity and at high yield.

The invention claimed is:

1. A compound of formula (I), or a stereoisomer or hydrate thereof:

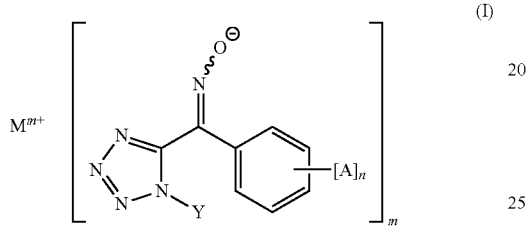
(I)

wherein,
A represents a halogen atom, alkyl group, haloalkyl group, alkoxy group, haloalkoxy group, alkylsulfonyl group, unsubstituted or substituted aryl group, cyano group, or nitro group,
n represents an integer of 0 to 5 (and A may be mutually the same or different when n is 2 or more),
Y represents an alkyl group,
M represents an alkaline metal or alkaline earth metal, and
m represents an integer of 1 or 2.

2. The compound according to claim 1, which is a (Z) form.

3. The compound according to claim 1, which contains 2 molecules of water per molecule thereof.

4. The compound according to claim 1, wherein M is an alkaline metal.

5. A method for producing a compound of formula (I), or a stereoisomer or hydrate thereof:

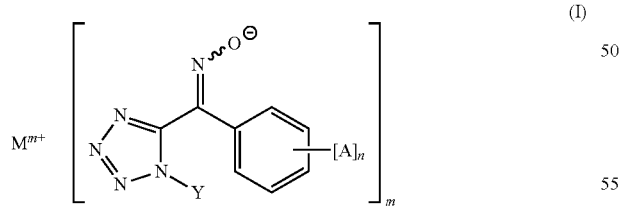
(I)

wherein,
A represents a halogen atom, alkyl group, haloalkyl group, alkoxy group, haloalkoxy group, alkylsulfonyl group, unsubstituted or substituted aryl group, cyano group, or nitro group,
n represents an integer of 0 to 5 (and A may be mutually the same or different when n is 2 or more),
Y represents an alkyl group,
M represents an alkaline metal or alkaline earth metal, and m represents an integer of 1 or 2, comprising:
step (A): allowing an alkaline metal compound or alkaline earth metal compound to act on a tetrazolyloxime derivative of formula (II):

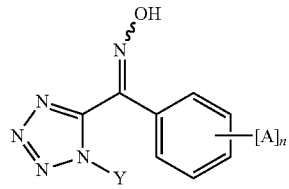
(II)

wherein, A, n and Y are the same as in formula (I).

6. A method for purifying a (Z) form of a compound of formula (I), or a hydrate thereof,
comprising:
step (B): crystallizing crystals of the (Z) form of the compound of formula (I), or a hydrate thereof by adding an alcohol to an aqueous solution of the compound of general formula (I):

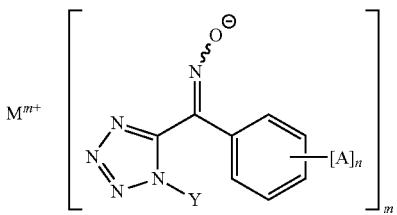
(I)

wherein,
A represents a halogen atom, alkyl group, haloalkyl group, alkoxy group, haloalkoxy group, alkylsulfonyl group, unsubstituted or substituted aryl group, cyano group, or nitro group,
n represents an integer of 0 to 5 (and A may be mutually the same or different when n is 2 or more),
Y represents an alkyl group,
M represents an alkaline metal or alkaline earth metal, and
m represents an integer of 1 or 2.

7. The purification method according to claim 6, wherein the alcohol is a lower alcohol.

8. A method for producing a (Z) form of a compound of formula (I), or a hydrate thereof,
comprising:
step (C): irradiating a solution containing an (E) form of the compound of formula (I):

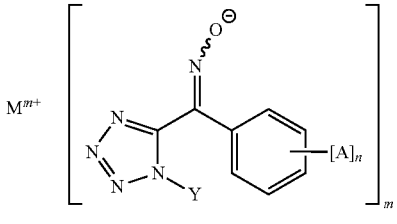
(I)

wherein,
A represents a halogen atom, alkyl group, haloalkyl group, alkoxy group, haloalkoxy group, alkylsulfonyl group, unsubstituted or substituted aryl group, cyano group, or nitro group, n represents an integer of 0 to 5 (and A may be mutually the same or different when n is 2 or more), Y represents an alkyl group, M represents an alkaline metal or alkaline earth metal, and m represents an integer of 1 or 2 with light and isomerizing to the (Z) form.

9. The method for producing the (Z) form of a compound of formula (I), or a hydrate thereof, according to claim 8, in which the solution containing the (E) form of the compound of formula (I) is an aqueous solution, further comprising step (B'): precipitating crystals of the (Z) form of the compound of formula (I), or a hydrate thereof, by adding an alcohol to the aqueous solution following the step (C).

10. A method for producing a tetrazolyloxime derivative of formula (IV), or a stereoisomer or hydrate thereof, comprising: step (D1): obtaining a tetrazolyloxime derivative of formula (IV) by reacting a compound of formula (I) with a halide of formula (III):

[Chemical Formula 6]

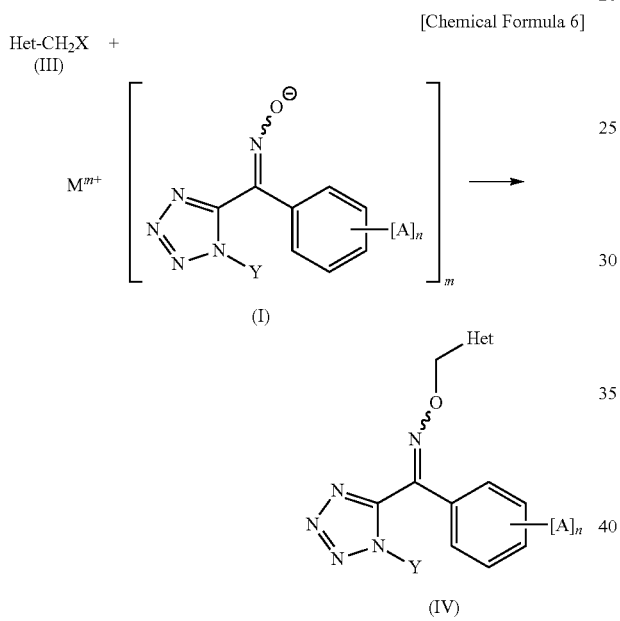

wherein, in general formula (III),

Het represents a substituted pyridyl group or substituted thiazolyl group, and

X represents a halogen atom, and in general formula (I),

A represents a halogen atom, alkyl group, haloalkyl group, alkoxy group, haloalkoxy group, alkylsulfonyl group, unsubstituted or substituted aryl group, cyano group, or nitro group, n represents an integer of 0 to 5 (and A may be mutually the same or different when n is 2 or more), Y represents an alkyl group, M represents an alkaline metal or alkaline earth metal, and m represents an integer of 1 or 2, and in general formula (IV), Het, A, n and Y are respectively the same as in general formula (III) and general formula (I).

11. The method for producing the tetrazolyloxime derivative of formula (IV), or the stereoisomer or hydrate thereof, according to claim 10, wherein the halide compound of formula (III) is a halogenated picoline derivative of formula (VI):

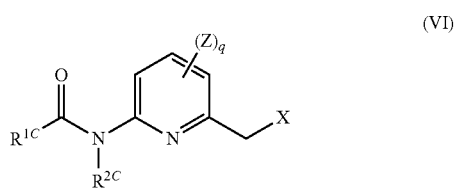

wherein, $R^{1C}$ represents an unsubstituted or substituted alkyl group or unsubstituted or substituted alkoxy group, $R^{2C}$ represents a hydrogen atom, unsubstituted or substituted alkoxycarbonyl group, or unsubstituted or substituted acyl group, X represents a halogen atom, Z represents a halogen atom, cyano group, nitro group, hydroxyl group, thiol group, formyl group, carboxyl group, unsubstituted or substituted amino group, unsubstituted or substituted alkyl group, unsubstituted or substituted alkenyl group, unsubstituted or substituted alkynyl group, unsubstituted or substituted aryl group, unsubstituted or substituted heterocyclic group, $OR^3$, $S(O)_pR^3$, $COR^3$ or $CO_2R^3$ (wherein, $R^3$ represents an unsubstituted or substituted amino group, unsubstituted or substituted alkyl group, unsubstituted or substituted alkenyl group, unsubstituted or substituted alkynyl group, unsubstituted or substituted aryl group, or unsubstituted or substituted heterocyclic group, and p indicates the number of oxygen atoms shown in parentheses and is an integer of 0 to 2), and q indicates the number of substituents Z and is an integer of 0 to 3, and a plurality of Z may be mutually the same or different when q is 2 or more.

* * * * *